United States Patent [19]

Macovski

[11] Patent Number: 4,565,968

[45] Date of Patent: Jan. 21, 1986

[54] BLOOD VESSEL PROJECTION IMAGING SYSTEM USING NUCLEAR MAGNETIC RESONANCE

[76] Inventor: Albert Macovksi, 2505 Alpine Road, Menlo Park, Calif. 94025

[21] Appl. No.: 466,969

[22] Filed: Feb. 16, 1983

[51] Int. Cl.[4] .......................................... G01R 33/08
[52] U.S. Cl. ..................................... 324/309; 324/306
[58] Field of Search .............. 324/300, 306, 307, 309, 324/311, 313

[56]  References Cited

U.S. PATENT DOCUMENTS 4,471,305  9/1984  Crooks ................................. 324/309
4,475,084  10/1984  Moore ................................. 324/309

Primary Examiner—Michael J. Tokar
Attorney, Agent, or Firm—Flehr, Hohbach, Test, Albritton & Herbert

[57] ABSTRACT

A two-dimensional projection image of the NMR activity within a volume is obtained. The signals due to static material are cancelled and do not appear in the projection image. The signals due to moving blood in vessels produce an isolated image of the vessels with the superimposed structure removed. The excitation of a plane is accomplished using a single excitation pulse without requiring an a.c. gradient. The uniformity requirement of the inversion excitation is minimized. Images are generated which distinguish the direction of flow.

25 Claims, 9 Drawing Figures

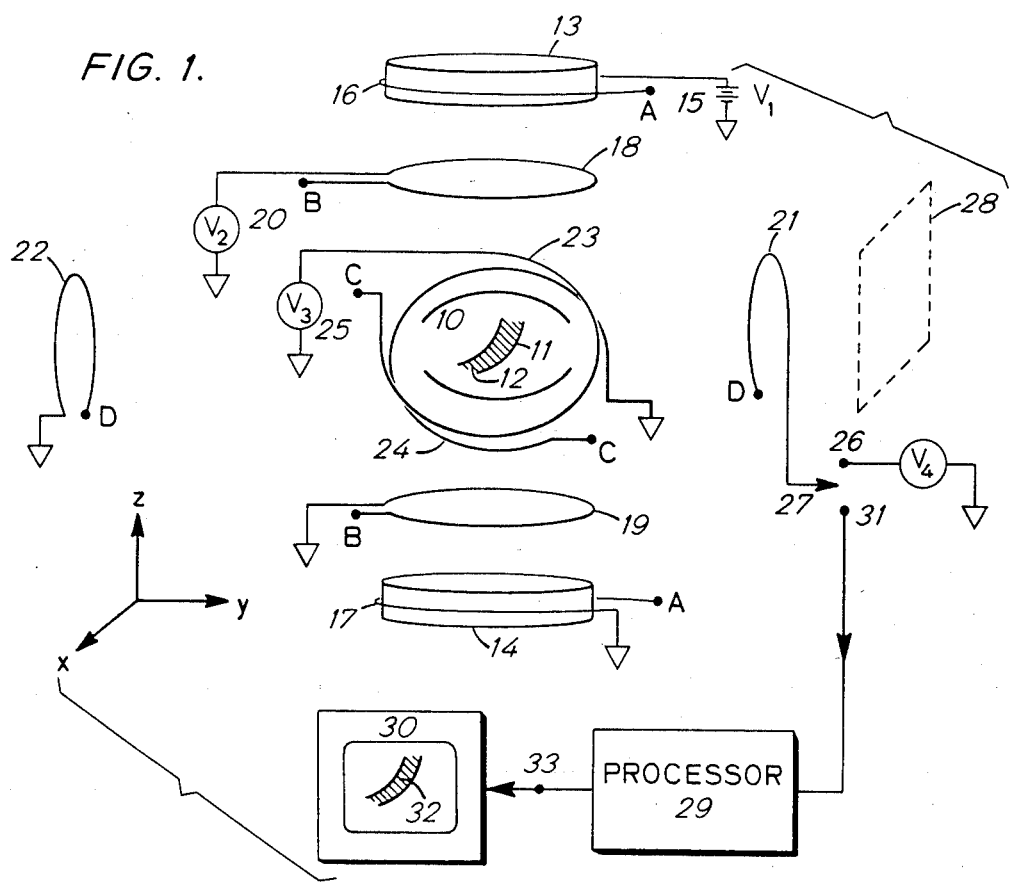

BLOOD VESSEL PROJECTION IMAGING SYSTEM USING NUCLEAR MAGNETIC RESONANCE

BACKGROUND OF THE INVENTION

1. Field of the Invention

This invention relates to medical imaging systems using nuclear magnetic resonance. In a primary application the invention relates to projection imaging of blood vessels by virtue of the moving blood within the vessels. Other applications include general projection imaging of moving materials.

2. Description of the Prior Art

Nuclear magnetic resonance, abbreviated NMR, represents a new approach to medical imaging. It is completely non-invasive and does not involve ionizing radiation. In very general terms, magnetic moments are excited at specific spin frequencies which are proportional to the local magnetic field. The radio frequency signals resulting from the decay of these spins are received using pick-up coils. By manipulating the magnetic fields, an array of signals are provided representing different regions of the volume. These are combined to produce a volumetric image of the density of the body.

A descriptive series of papers on NMR appeared in the June 1980 issue of the IEEE Transactions on Nuclear Science, Vol. NS-27, pp. 1220-1255. The basic concepts are described in the lead article, "Introduction of the Principles of NMR" by W. V. House, pp. 1220-1226.

A number of three-dimensional methods are described. One important one is described by P. V. Lauterbur and C. M. Lou entitled, "Zeugmatography by Reconstruction from Projections," pp. 1227-1231. In this approach, a linear field gradient is superimposed on the strong axial magnetic field. As a result of the gradient, each plane in the volume, in a direction normal to the gradient, experiences a different resonant frequency. A burst, containing a spectrum of frequencies, is used to simultaneously excite each of the planes. The received signal, following the excitation, is then Fourier transformed into its individual components. The amplitude at each frequency representing a planar integration of the proton density. This process can be repeated using a gradient field in different directions to collect information about arrays of planes. These planar integrals can be used to produce two-dimensional projection images of a volume or, alternatively, three-dimensional information about the proton density of each voxel in the volume.

The projection image is obtained by obtaining the integrated density of substantially all planes which are normal to the plane of the projection image. The total number of planes required, at all angles and positions, is substantially equal to the number of pixels in the two-dimensional projection image. The reconstruction procedure involves the classical reconstruction from projections widely used in current computerized tomography systems. The most generally used procedure is that of convolution-back projection.

The resultant two-dimensional projection images have a number of drawbacks as regards the imaging of vessels. Firstly, the superimposed intervening structures make it very difficult to visualize the vessels and diagnose stenosis or narrowing. Secondly, the nature of this imaging procedure is such that all of the measurements affect every reconstructed pixel. This makes the image particularly sensitive to motion. Any motion of the object will cause artifacts in the image due to inconsistencies where the object does not match its projections. These artifacts can often obscure the desired information.

To avoid the problems of intervening structures, three-dimensional reconstructions are made which provides cross-sectional images. The approach taken in the Lauterbur paper involves making an array of two-dimensional projection images at every angle through the object. Lines in these projection images represent line integrals or cross-sectional planes of the object. Thus, again using classical reconstruction techniques, any desired cross-sectional plane can be reconstructed. The intermediate two-dimensional projections are not used for the reasons discussed.

Although these cross-sectional images are free of intervening structures, they are unsuitable for vessel imaging. Vessel imaging, no matter what the modality, x-ray or NMR, is best done with two-dimensional projection images. Cross-sections merely show slices through the vessels. In addition, the acquisition of three-dimensional data takes a relatively long time, thus resulting in a variety of artifacts due to the various physiological motions of the body.

A second general method of acquiring and processing NMR imaging data is described in a paper by E. R. Andrew entitled "Nuclear Magnetic Resonance Imaging: The Multiple Sensitive Point Method" pp. 1232 to 1238 of the same issue. In this method, a selective system is used which acquires data from individual voxels in the volume of interest. This is accomplished using dynamically varying fields for the gradients. In general, with these dynamic fields, all but the small region not containing the time-varying field integrates to zero. Thus, if time varying fields of different frequencies are applied to three orthogonal axes, only a single point of voxel will not be time-varying. The signal will therefore represent solely that point without requiring reconstruction from projections.

The difficulty with this system is that it requires a very long data acquisition time since the signal is taken from one voxel at a time. Sufficient time must be spent at each voxel to provide an adequate signal to noise ratio. This problem is alleviated by using dynamic gradients on two axes and a static gradient on the third axis. Thus, in the direction of the third axis, each position again corresponds to a different frequency. Using wideband excitation and Fourier transforming the received signal the frequency spectra simultaneously provide the density of an array of voxels along a line. The line is that corresponding to the intersection of the two orthogonal dynamic gradients where all but a single line averages to zero.

Although the method avoids the motion artifacts caused by reconstruction from projections, it continues to provide a relatively long data acquisition time with the resulting blurring from physiological motions including respiratory and cardiovascular. In addition it is a three-dimensional imaging system which, as has been described, is generally unsuitable for vessel imaging.

A third imaging method is also line or point selective and is described in a paper by L. E. Crooks entitled, "Selective Irradiation Line Scan Techniques for NMR imaging" of pp. 1239-1244 of the same issue. This general approach has a number of variations. In one, a selective pulse is used to excite a single plane of interest using a static gradient and an appropriately shaped pulse. The resulting signal from the excited plane is stored. Following equilibrium an orthogonal plane is excited with a higher intensity such that the magnetization is inverted or made negative. Irradiation of this type produces no received signal. The first step is then repeated by selectively exciting the plane of interest and storing the resultant signal. In this case, however, a line in the plane of interest will be missing since it has been saturated by the high intensity excitation of a plane orthogonal to the plane of interest. Thus the line of intersection is not included in the resultant signal. A simple subtraction of the first and second stored signals represents the line of intersection. By measuring different lines at many angles and positions in the plane of interest, using this subtraction procedure, a reconstructed image of the plane is made using classical reconstruction from projection techniques.

An alternative approach using the same line intersection of orthogonal planes avoids the subtraction operation. In this case the orthogonal plane is immediately excited with inverting radiation. The line of intersection is affected so as to produce a spin echo signal at a later time. Thus, at this later time, the signal represents the desired line only. Again, an array of line integral signals are used to provide a cross-sectional image.

Similar sensitive point and sensitive line methods have been suggested which results in saturation of all but a specific plane of interest. This is immediately followed by a similar excitation in an orthogonal direction which saturates everything in the plane except a line. Either the line integral signal can be acquired, or a third orthogonal excitation can be used to acquire the signal from a point or voxel. Saturation is achieved by a relatively long "burn" radio frequency pulse, in the presence of a gradient, which demagnetizes the region corresponding to the frequencies excited. This procedure is described in a paper by A. N. Garroway, P. K. Grannell and P. Mansfield, "Image Formation in NMR by a Selective Irradiative Process," which appeared in J. Phys. C: Solid State Physics, Vol. 7, 1974, pp. L457–L462.

An additional approach to NMR imaging is described in a recent book entitled *Nuclear Magnetic Resonance Imaging In Medicine*, published in 1981 by Igaku-Shoin, Ltd., Tokyo. Chapter 3 of this book, by Lawrence E. Crooks, provides an overview of the various imaging techniques. In addition to those already mentioned there is another planar integration approach described on pp. 44–47. Here, each plane integral is phase encoded by applying a gradient normal to the plane. When the gradient is removed, the nuclei along the plane have cyclical phase distributions, depending on the strength of the magnetic field. By acquiring these planar integrals using phase distributions with different spatial frequencies, information is acquired about each line in the plane. This information is decoded again using Fourier transforms. This approach has been termed spin warp imaging.

Another approach has recently been reported on, which also provides cyclical distributions along a plane. In this case, however, the cyclical variations are achieved by imposing a gradient on the intensity of the r.f. excitation field. If the gradient is made strong enough, cyclical variations will occur across the plane where the regions of 90° excitation will provide a maximum response and those of 0° and 180° will have no response. As before, a series of excitations with gradients of varying intensities provides cyclical variations at different spatial frequencies which can be transformed to reconstruct the distribution within the selected plane. This process is described in a paper by D. I. Hoult entitled, "Rotating Frame Zeugmatography," which appeared in Phil. Trans. R. Soc. London, B289:543–547 (1980).

All of the NMR imaging systems that have been reported on are unsuitable for vessel imaging for a number of previously indicated reasons. Firstly, all but the first technique have been used to provide three-dimensional cross-sectional images which are unsuitable for vessel imaging. The vessel will wind through many planes, such that each cross section is of limited value. Projection imaging, as presently practiced in x-ray angiography, has been clearly shown to be the preferred modality for diagnosing narrowing or stenosis in vessels. In the one case where projection NMR imaging has been considered, as in the system of the first paper cited, the intervening tissue would seriously reduce the effectiveness of the image. In addition, these images require very long data acquisition times and produce severe artifacts due to object motion.

A paper on flow measurement written by J. R. Singer entitled, "Blood Flow Measurements by NMR of the Intact Body," appeared on pp. 1245-1249 of the previously mentioned IEEE Transactions on Nuclear Science. In this paper the concept of phase shift of the spin echo being proportional to average velocity is presented. Singer proposed to use both phase sensitive and envelope detection to map the proton density and flow of an entire volume using three-dimensional imaging techniques. The resultant cross-sectional images would show both density and flow. As before, the principle difficulty with these images are the very long data acquisition time, with its associated distortions, and the relative inability to diagnose vessel disease with cross-sectional images.

An additional imaging sequence, described in a paper by I. R. Young, et. al., entitled "Magnetic Resonance Properties of Hydrogen: Imaging the Posterior Fossa," Amer. Journal of Radiology, Vol. 137, pp. 895–901, November 1981, and used in many of the present commercial instruments for cross-sectional imaging, involves a single excitation burst to select the desired plane. This burst takes place in the presence of a gradient in the z direction. Thus the burst frequency selects a specific xy plane in the volume. Immediately following the burst, when the FID signal is being received, the z gradient is turned off and a transverse gradient is applied. This results in each line in the plane, normal to the transverse gradient, generating a different frequency. For cross-sectional imaging this sequence is repeated with the transverse gradient rotated to different angles. For projection imaging, the subject of this application, only a single excitation in the presence of a transverse gradient is required to obtain the projection of the particular excited plane.

In systems requiring a spin version, such as the widely used inversion-recovery sequences, the result can be distorted if the 180° inversion is not uniformly produced throughout the region. This can be caused by inhomogeneity of the r.f. field. To minimize this problem the inversion excitation can be provided by adiabatic fast passage or AFP. This is described in pages 17-20 of the book Experimental Pulse NMR by E. Fukushina and S. B. W. Roeder and published by Addison-Wesley. To accomplish the inversion the frequency is swept through resonance at a rate such that no appreciable relaxation takes place during the sweep. The net result is a 180° inversion which is relatively insensitive to the field homogeneity.

U.S. Patent application Ser. No. 332,925, by the same inventor, covered the basic concept and methods for producing a two-dimensional projection image of the moving material in a volume. This is a highly desirable modality for imaging blood vessels. The application showed a number of methods for imaging solely the moving material and cancelling the static material. These included a 180° inversion signal, a two-burst inversion signal, the subtraction of signals acquired at different times representing different velocities, the receiving of signals adjacent to the region being excited and the use of the phase shift resulting from moving nuclei.

The application also described a variety of methods of providing a projection image. One of these involved the excitation of a plane, and then the decomposition of the plane into the required array of line integrals. In the method described, using a single excitation, an a.c. gradient signal was used to isolate the plane. This approach, for some of the moving material imaging technique, is somewhat difficult in that high frequency a.c. gradient signals can require significant amounts of power.

Also, the moving material imaging technique using a 180° inversion signal can be unduly critical. Any departure from 180° excitation produces a free induction decay signal for static material, thus failing to cancel the intervening tissue.

The application did not specifically show methods of distinguishing the direction of blood flow. This can be important in the distinguishing of arterial and venous flow. For example, in imaging the vessels leading to the brain it can be important to distinguish the carotid arteries from the jugular veins, to avoid the overlapping images.

SUMMARY OF THE INVENTION

An object of this invention is to provide an NMR projection image of vessels within the body.

A further object of this invention is to provide a projection image of vessels using a technique of planar excitations which requires only a single excitation and does not require high power a.c. gradient signals.

A further object of this invention is to provide a projection image of vessels where the excitation requirements for cancelling the static materials is not critical.

A further object of this invention is to provide a projection image of vessels indicating the direction of flow, enabling veins and arteries to be distinguished.

Briefly, in accordance with the invention, a two-dimensional projection image is created of the magnetic spins in a volume. Those magnetic spins due to static materials are cancelled. The magnetic spin signals due to moving materials remain forming a two-dimensional projection image of the blood vessels in the body. A planar excitation followed by a transverse gradient simplifies the collection of the projection of each plane. Saturation excitation and adiabatic fast passage reduces the critical nature of field uniformity. Excitation of a plane, and the reception of signals above and below the plane, distinguishes the direction of flow.

BRIEF DESCRIPTION OF THE DRAWINGS

For a more complete disclosure of the invention, reference may be made to the following detailed description of several illustrative embodiments thereof which is given in conjunction with the accompanying drawings, of which:

FIG. 1 is a schematic drawing illustrating an embodiment of the invention;

FIGS. 2A and 2B are portions of a block diagram of an embodiment of the invention involving subtraction of image information derived at different times;

DESCRIPTION OF THE PREFERRED EMBODIMENT

Figure 2B:
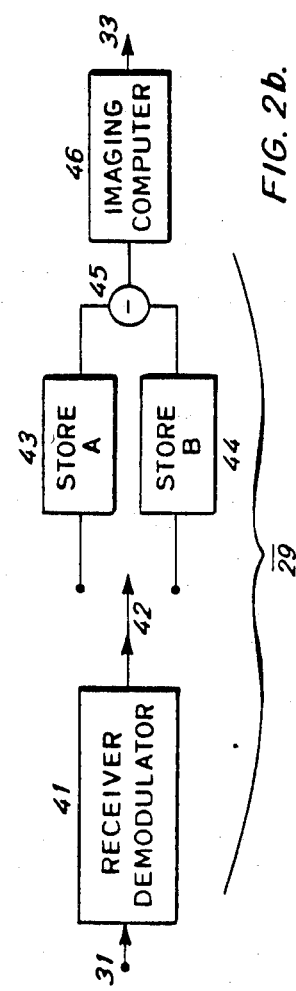

An understanding of the broad aspects of the invention may best be had by reference to FIG. 1. Here it is desired to provide an image of blood vessel 11 in a particular volume 10 of the human anatomy. Vessel disease is by far the most prevalent cause of death in humans. What is greatly desired in a noninvasive method of visualizing the vessels so as to provide mass screening of the general population. A process of this type requires the production of projection images of the vessels. This is in sharp contrast to existing x-ray computerized tomography or NMR cross-sectional images. These slices are of little value in evaluating narrowing in vessels since it requires a large array of them to follow a vessel. Clearly, the cross-sectional format is of little value in providing screening images for vessel disease. Also, NMR cross-sectional images are particularly sensitive to artifacts caused by non-uniform magnetic fields.

Therefore, in this invention, projection images of the vessel are created. For example, a two-dimensional projection image is made of volume 10 containing vessel 11. This projection can be represented by plane 28 in an xz plane.

A pure projection image would fail to visualize vessel 11 due to all of the intervening anatomical structures. In x-ray studies the vessels are isolated by injecting a contrast material. In this invention, using NMR imaging, an isolated projection image is made of vessel 11 by making used of the flowing motion of blood 12 through the vessel. Processor 29, in conjunction with r.f. excitation signal 26, operates to cancel the spin signals produced by the relatively static material in volume 10 and thus provide a signal solely due to vessel 11. In this way, the desired projection image is created in a totally noninvasive manner without any injection of contrast agents or use of ionizing radiation.

The description of the specifics of the NMR projection imaging will follow the description of the cancellation of the static material in volume 10. In general, however, the principal axial magnetic field is produced using, for example, pole pieces 13 and 14 excited by coils 16 and 17. These are driven by a d.c. source $V_1$ with the coils 16 and 17 producing fields in the same direction to create a substantially uniform field throughout the region of interest in volume 10. This is by far the strongest field in the system with a strength of the order of one kilogauss. With both this coil and the remaining coils, the letter pairs A-D are simply convenient ways of indicating connections.

Specific regions are selected using the gradient coils. Coils 18 and 19 form a gradient field in the z direction driven by 20, source $V_2$. Similarly coils 23 and 24 are on opposite sides of object 10 and thus form a gradient field in the x direction driven by 25, source $V_3$. Unlike coils 16 and 17 which create a uniform field, these gradient coils are bucking each other so as to produce a varying field in the respective direction.

Coils 21 and 22 are the radio frequency coils serving both the transmitter and receiver function. They produce fields in the same direction to create a substantially uniform field in volume 10. When switch 27 is in the transmit position 26, generator $V_4$, is used to excite the magnetic spins in volume 10. When switch 27 is connected to the receive position, signal 31 is received from magnetic spin signals in volume 10. These are processed in processor 29 to provide a projection image of the moving blood 12 in vessel 11. The resultant projection image 32 is displayed in display 30.

Excitation signal 26, and processor 29 combine to cancel or eliminate any magnetic spin signals due to structures in object 10 which are substantially static. One method of eliminating the signals due to the magnetic spins of static materials is illustrated in FIGS. 2A and 2B. Here the magnetic spins are excited, and signals are received at two different time intervals $T_A$ and $T_B$. These correspond to time intervals where the blood velocity is different. The usual r.f. excitation signal 26, $V_4$, is supplied by burst generator 40. The specifics of the pulse shape depend on the particular imaging arrangement used. In any case two bursts are generated at the two time intervals.

Moving blood, or other material, can result in a decrease in the received NMR signal since the excited spins move out of the sensitive region before they result in received signals. Thus a high velocity region will produce a smaller signal than a low velocity region. By timing the excitation signal $V_4$ with the EKG of the patient under study, received signals 31 can be collected representing times of relatively high and low velocity of blood 12 in vessel 11. The received signals 31 are demodulated using demodulator 41 and applied to switch 42 which is also activated at $T_A$ and $T_B$ by the EKG signal. Thus the signal from excitation $T_A$ is stored in 43, store A, and the signal from excitation $T_B$ is stored in 44, store B. These are subtracted in subtractor 45 to provide the desired signal representing vessels only and cancelling all static material. The subtracted signal is applied to imaging computer 46 which, as will subsequently be described, reconstructs a two-dimensional projection image.

Signals due to any substantially static material will be cancelled since the component signals will be the same at $T_A$ and $T_B$. The signals from vessel 11, however, will be different since they are taken with the blood 12 at different velocities.

Although FIGS. 2A and 2B illustrate a specific embodiment, this same principle can be applied in many ways. For example, a sequence of pulses 26 can be produced all representing the time $T_A$ in the heart cycle. This sequence of pulses may be required to generate a complete projection image corresponding to the $T_A$ time interval. This is followed by a sequence at $T_B$ in the heart cycle. The subtraction operation can then involve the complete image information rather than apply the subtraction at each heart cycle. In any case, it is desirable for the vessel to be at a similar position in $T_A$ and $T_B$ to avoid any loss of information.

The description thusfar has been identified to that of the basic concept covered in U.S. application Ser. No. 332,925. However, in the description of the rapid projection imaging system, where each plane in sequence is decomposed into a set of integrals either an a.c. gradient or multiple excitations are used. Although these are excellent methods of imaging, it is often desirable to use simpler systems. To accomplish this we use a projection imaging system similar to that employed in some cross-sectional imaging systems which requires only a single r.f. excitation without an a.c. gradient.

First, in the presence of a z gradient a 90° r.f. burst, of a specific frequency is applied, exciting the spins in a specific xy plane. Immediately following the burst, during the time the FID is received, the z gradient is turned off and a transverse gradient is applied. Thus each line in the excited plane, normal to the transverse gradient, produces an FID signal of a different frequency. Decomposing the composite received FID signals into their component frequencies provides the desired line integrals or projection of the plane in a direction normal to the transverse gradient. This process is repeated at each planar section, using a different excitation frequency, providing the desired two-dimensional projection image of the entire volume. This projection imaging approach is less complex than those described in U.S. application Ser. No. 322,935. The high power a.c. gradients or multiple excitations are not required.

Figure 3:
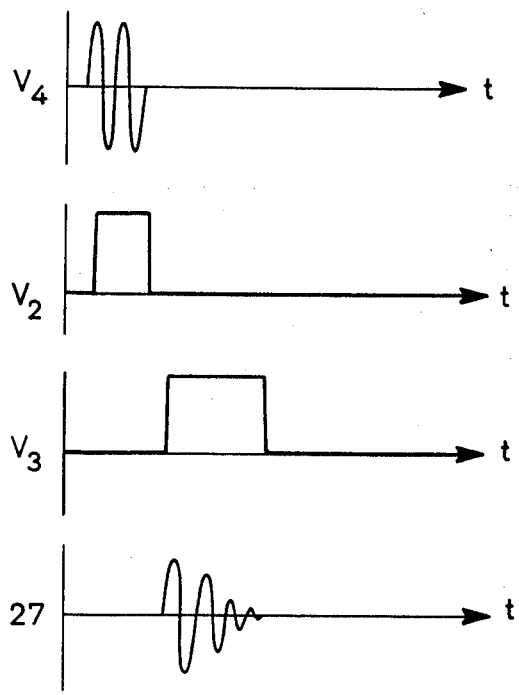
FIG. 3 consists of waveforms of the signals used and received in an embodiment of the invention.

Referring to FIG. 1 and the waveform diagram in FIG. 3, with the B terminal on gradient coil 18 connected to the B terminal on gradient coil 19, a pulsed gradient signal 20 is applied using $V_2$. Simultaneously, with terminal D on r.f. coil 21 connected to terminal D on r.f. coil 22 and switch 27 in the receive position, connected to 26, a high frequency burst $V_4$ is applied of appropriate amplitude and duration to provide the classic 90° excitation. Following this burst signal the gradient signal $V_2$ is turned off, the transverse gradient signal 25 is turned on where terminal C on coil 23 is connected to terminal C on coil 24 and $V_3$ is pulsed on during the FID signal interval. During this same interval switch 27 is connected to terminal 31 so that the received FID signal can be processed by processor 29. In this case processor 29 is a frequency decomposition system, such as a computerized Fourier transform, where the FID signal is decomposed into its constituted frequencies, each representing a line integral in the y direction, of the selected xy plane.

The entire process is repeated using different burst frequencies for $V_4$, thus selecting xy planes at different z positions, each time determining the line integrals or projections of the xy plane onto projection plane 28.

This provides the entire two-dimensional projection 32 displayed on 30.

However, it is desired to use this efficient projection imaging system to display only the moving material in vessels and therefore to cancel all moving material. One approach is to use aforementioned temporal subtraction system illustrated in FIGS. 2a and 2b. Here the signals obtained from the excitations at different portions of the heart cycle are stored and subtracted. This can directly be applied to the projection system diagrammed in FIG. 3.

The projection system of FIG. 3 can also be applied to the inversion technique described in U.S. application Ser. No. 332,935. Here, instead of a 90° excitation, $V_4$ becomes a 180° excitation by doubling either the signal amplitude or time or some appropriate combination. A 180° inversion produces no free induction decay signal, thus cancelling the signal from all moving material. The moving blood in vessels, however, does not experience a complete inversion, thus producing an FID signal. Therefore the system of FIG. 3 produces solely the desired projection image of moving blood and provides vessel image 32 on display 30.

This single excitation projection system does offer simplicity in that it minimizes the r.f. power and does not require an a.c. gradient signal. Its snr performance, however, is poorer than the dual excitation approach described in U.S. Ser. No. 332,925. Using the 90°–180° sequence produces a spin echo rather than an FID, thus doubling the duration of the signal and increasing the snr. For the inversion system the sequence becomes 180°—180° as shown in U.S. Ser. No. 332,925 where static material is cancelled and only moving blood provides an echo.

Figure 4:
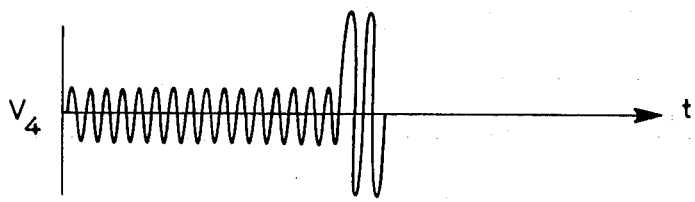
FIG. 4 consists of a waveform of the r.f. excitation signal for an embodiment of the invention.

One difficulty with the invention excitation system is the accuracy required to cancel all static material. If the r.f. fields produced by coils 21 and 22 are not uniform, portions of the object 10 will not experience an exact inversion and thus produce an FID signal which will appear in display 30. If this signal is excessive it can obscure the desired image 32 of vessel 11 resulting from the movement of blood 12. One approach to minimizing the uniformity requirements of the r.f. field is the use of a saturation or "burn" excitation followed by a 90° burst for the excitation signal as shown in FIG. 4. Here a low level excitation, comparable in time to $T_1$, is used to saturate the spins in the excited region so as to insensitize them. This procedure is described in the previously referenced paper by A. N. Garroway, et al., "Image Formation in NMR by a Selective Radiation Process." This saturation excitation, as shown in FIG. 4, is immediately followed by a 90° burst. Saturated regions, representing static material, will be unresponsive and produce no FID signal. Moving blood, however, which has not been completely saturated, will produce an FID signal and an image. This signal $V_4$, shown in FIG. 4, simply replaces the 90° excitation in FIG. 3, as did the 180° inversion signal.

The use of a saturation signal followed by a 90° burst can replace a 180° inversion excitation in all of the projection imaging embodiments of U.S. application Ser. No. 332,925 and provide the desired immunity to nonuniformity. This includes the spin warp, multiple plane and all other projection systems where an inversion excitation can be used to cancel static material and image only moving material.

One difficulty with the saturation −90° excitation is its increased time duration, since the saturation signal is comparable to $T_1$. It may be helpful to time the repetitive signals in synchronism with the electrocardiogram to avoid the problem of moving vessels.

Figure 5:
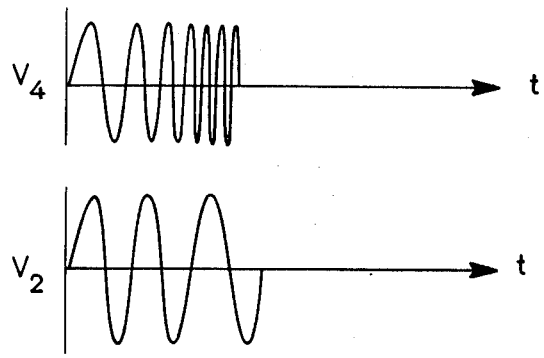
FIG. 5 consists of waveforms of the signals for an embodiment of the invention using adiabatic fast passage excitation.

The problem of long imaging time, however, can be overcome by the use of a adiabatic fast passage or AFP excitation where an inversion is achieved by sweeping the r.f. signal $V_4$ through resonance. This excitation is also relatively immune to nonuniformity of the r.f. field. Unfortunately, the previously described projection imaging system cannot be directly applied since the swept frequency, of itself, cannot be used for plane selection. The a.c. gradient system can, however, be used in combination with the AFP excitation signal as shown in FIG. 5. Here, while $V_4$ has the swept r.f. signal, an a.c. gradient signal is applied to $V_2$. The null plane of this a.c. gradient signal will be the only plane receiving excitation. The null plane is readily varied by varying the relative excitation of coils 18 and 19. By grounding B on coil 18 and connecting a signal $kV_2$ to terminal B on coil 19, the null plane can be varied by varying k, where k=1 provides a null plane between the two coils. Following excitation of the desired plane with an inversion signal, the signals are read out as before in FIG. 3 using a transverse gradient $V_3$. This approach provides a stable method of inversion in a relatively short time interval.

In many clinical situations it is desired to distinguish venous from arterial flow. One approach to this is the temporal subtraction method of FIGS. 2a and 2b. Since arterial blood has a stronger pulsatile component, using appropriate timing, an image can be made of solely the arteries, ignoring the veins, which have a weaker pulsatile component of velocity.

Figure 6:
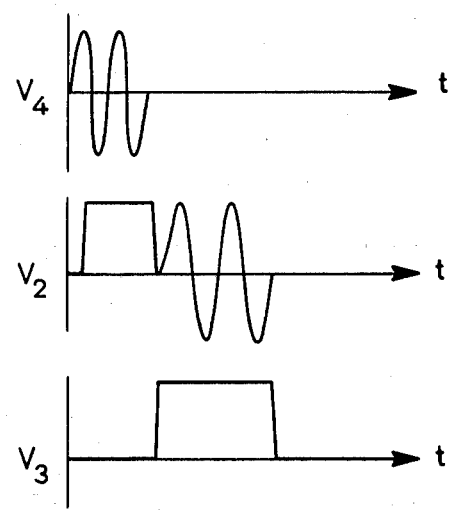
FIG. 6 consists of waveforms of the signals for an embodiment of the invention having flow direction sensitivity.

Another approach is to distinguish between venous and arterial flow by virtue of their directions. For example, in imaging the vessels in the neck, the carotid arteries carry blood upward into the brain while the jugular veins carry blood downward, back toward the heart. If an xy plane is excited and the received signals are gathered in a plane solely above or solely below the excited plane, the two directions can be distinguished. Thus an excitation of an xy plane, using a 90° burst for $V_4$ in the presence of a z gradient, as shown in FIG. 6 can be followed by an a.c. gradient whose null plane is either above or below the excited plane. Again, the signal from this null plane is read out in the presence of a transverse gradient $V_3$ to decompose the lines of the plane into different frequencies. Only moving material which has flowed from the excited plane to the null plane, above or below the excited plane, will produce signals contributing to vessel projection image 32. This sequence is repeated for all planes in the volume to complete the image.

Figure 7:
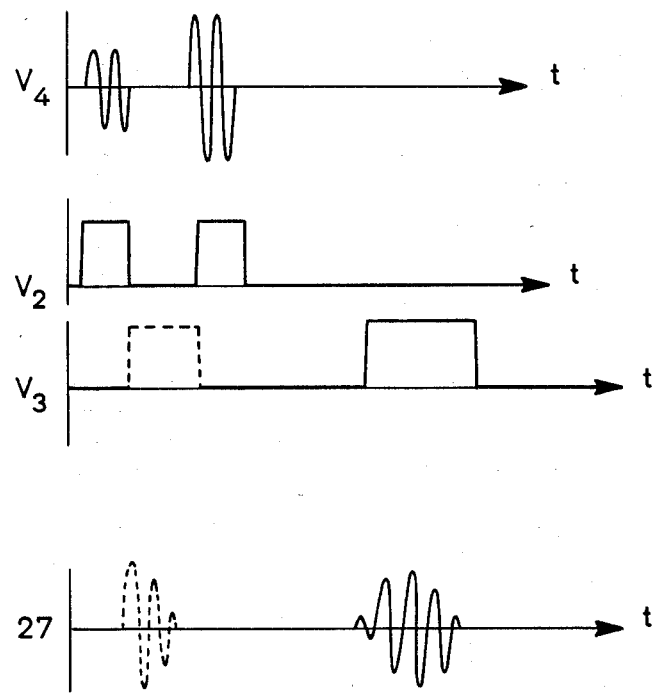
FIG. 7 consists of waveforms of the signals for an embodiment of the invention using dual-excitation to obtain flow direction sensitivity.

The use of the a.c. gradient in direction-sensitive vessel imaging can be avoided using the dual excitation method of FIG. 7. Here upward or downward flow is selected by utilizing spin echo excitation where the 180° excitation corresponds to planes above or below the initial excited plane. As shown a 90° excitation is first used on $V_4$ in the presence of a z gradient $V_2$ to excite the desired plane. The FID, shown in dotted lines, following this excitation is ignored since it represents signals from static material. With the z gradient $V_2$ turned on again, a 180° excitation is applied on $V_4$ following a relatively brief time interval. This 180° excitation is slightly lower or higher in frequency than the 90° excitation. Moving material, such as blood, which has migrated from the 90° excited plane to the 180° excited plane will produce a spin echo signal in 27. During this spin echo, as shown in FIG. 7, the transverse gradient $V_3$ is turned on to decompose the selected plane into an array of lines to create the desired projection. This process is repeated using different frequencies for the $V_4$ bursts, where every 180° burst is correspondingly slightly higher or lower in frequency than the 90° burst, depending on whether an image of upward or downward flow is desired. Both images can be obtained in sequence if desired.

Figure 8:
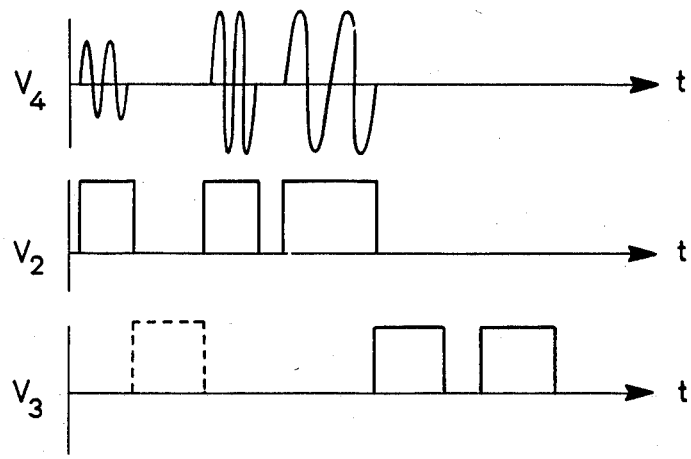
FIG. 8 consists of waveforms of the signals for an embodiment of the invention for simultaneously acquiring information of both flow directions.

In FIG. 7, either upward or downward flow was selected based on the frequency of the 180° burst with respect to the 90° burst. By using two 180° bursts, resulting in two spin echoes, as shown in FIG. 8, the signals representing upward and downward flow can both be collected from the same 90° excitation. These are non-interacting since they represent different nuclei in each case. As shown in FIG. 8, the 90° burst is followed by first a higher frequency 180° burst then a lower frequency 180° burst. These, depending on the direction of the z gradient, can for example represent the upper and lower planes respectively. They each produce separate spin echoes as shown. These are received in the presence of a transverse gradient $V_3$ to enable decomposition and the forming of the desired projection images. These each represent separate upward and downward flow images. As previously described in FIG. 7, the dotted waveforms can be used to provide an image of static material which can be used to either combine with the flow images, or correct them for the residual signals due to overlap of the excited planes. This overlap can be minimized by shaping the excitation pulses into sinc waveforms which approximate planar sections, as has been extensively discussed in the nmr literature.

The dotted FID following the 90° burst in FIGS. 7 and 8 can be used to enhance the images. If $V_3$ is also turned on during that first FID, as shown in the dotted line, the signal can again be decomposed to produce a projection image of the static material in the volume. This can be useful in producing a composite image where, for example, the static anatomic image is in one color and the moving blood in another. In addition, the planes selected by the 90° and 180° excitations may overlap somewhat. Thus the spin echo will contain some signal representing static structures due to the overlap of the two planes. The signal from the first FID, representing static material only, can be processed as previously described and used to cancel that part of the image which is due to static material caused by overlap of the planes. Each signal, the FID and the spin echo, are put through identical Fourier transform processing to find the line integrals of each plane as has been previously described.

Figure 9:
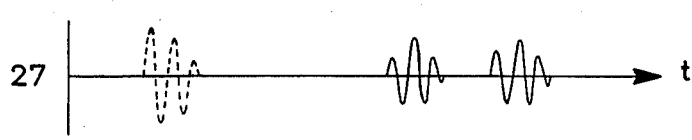
FIG. 9 consists of a block diagram illustrating an embodiment of the invention for combining static and flow images.

This is illustrated in FIG. 9 which illustrates a representative processor 29. Here the received signal 27 or 31 is applied to gating circuit 50 which gates out the FID representing the static material, and one or both of the spin echoes representing the directional flow signals. These are decomposed using Fourier transformers 51 and 52 to create the projection images. These static and flow images are combined in combiner 53 to either create a composite image showing static anatomy plus the flowing blood, or to create an accurate flow image where the residual static image information is subjected.

The methods described using FIGS. 7 and 8 for imaging directional flow can also be used for imaging flow independent of direction. Referring to FIG. 7, if the first burst $V_4$ is made a 180° narrow-band plane selection signal, and the second burst is a broadband 180° burst, the spin echo will then represent a flow image if processed as previously described. In essence, only moving material which experiences a partial excitation with the first burst, having a 90° component, will result in a spin echo. The broadband 180° second burst inverts the spins of all moving material, no matter where it has moved. The first 180° burst is shaped, based on anticipated flow. For example, assume blood is traveling in a large artery at about 50 cm/sec and the slice thickness of the excited plane is about 2 mm. It will therefore take about 4 millisec for a moving blood particle to traverse the excited plane. Therefore, if the first 180° burst has a width of about 4 milliseconds, on the average the moving material will receive a 90° excitation due to blood in the center of the excited region receiving only half of the total 180° inversion. Of course, some blood will receive less than 90° and some more. These will also produce partial spin echoes. The static material, however, will receive a complete inversion. As previously indicated, for reduced sensitivity to uniformity of the r.f. field, the first 180° pulse can be changed to a saturation excitation followed by a 90° pulse as in FIG. 4, or an adiabatic fast passage in the presence of an a.c. gradient, as in FIG. 5.

All of the many methods shown in the literature for enhancing the performance of nmr imaging systems can be applied to this blood vessel imaging system. For example, in the paper by P. A. Bottomley, "NMR Imaging Techniques: A Review" in the *Review of Scientific Instruments*, Vol. 53, September 1982, pp. 1319–1337, a method is shown known as "time reversal" which involves reversing the sign of the gradient pulses for a short period in order to obtain optimum sensitivity. This can clearly be applied to the appropriate gradient signals used in this invention.

What is claimed is:

1. In a method for producing a two-dimensional projection image of moving material in a volume using nuclear magnetic resonance the steps of:
    insensitizing the magnetic spins in a region of the volume using saturation excitation;
    exciting the spins in the region with a burst so that only moving material that has traveled into the region and not experienced complete saturation will produce an output signal; and
    processing the output signals to produce a two-dimensional projection image of the volume.

2. The method as described in claim 1 where the step of producing the two-dimensional projection image of the volume includes the steps of:
    applying a first gradient so that the saturation excitations and burst excitations excite a planar region in the volume;
    applying a second gradient, normal to the first gradient following the burst excitation so that each line integral in the planar region will produce a different frequency;
    decomposing the output signal into its constituent frequencies to provide the intensity at each point along the line represented by the planar region; and
    repeating the sequence using different frequencies for the saturation and burst excitations to provide the set of line integrals for each planar region in the volume.

3. In a method for providing a two-dimensional projection image of the moving material in a volume using nuclear magnetic resonance the steps of:

applying a first magnetic gradient field;

exciting the nuclear magnetic resonant spins in a planar region of the volume normal to the direction of the first gradient field;

applying a second magnetic gradient field normal to the first magnetic gradient field following the excitation signal during the time that free induction decay signals are received;

processing the free induction decay signals to provide a projection of only the moving material in the planar region of the volume; and repeating the sequence using different excitation frequencies in the presence of the first gradient field to excite the spins in different planar regions of the volume to complete the two-dimensional projection image of the volume.

4. The method as described in claim 3 where the step of exciting the nuclear magnetic spins in each planar region takes place when the moving material is at a first velocity and including the steps of:

repeating the process at each planar region where the moving material is at a second velocity; and subtracting the processed signals to cancel all static material.

5. The method as described in claim 3 where the step of exciting the nuclear magnetic resonant spins in a planar region of the body represents an inversion excitation whereby all static material produces no free induction decay signals.

6. The method as described in claim 3 including the step of applying an alternating gradient field in the same direction as the first gradient field during the time of the free induction decay signal where the null plane of the alternating gradient field is adjacent to the excited planar region whereby only moving excited nuclei which have traveled into the null plane will produce output signals.

7. In a method for producing a two-dimensional projection image of material flowing in a given direction in a volume the steps of;

exciting the nuclear magnetic spins in a planar region in the volume;

receiving signals from those nuclei which have moved to the upper or lower adjacent plane in the volume;

repeating the sequence for all planar regions of the volume; and processing the signals from each planar region to produce a two-dimensional projection image of moving material which has moved either upward or downward with respect to each planar region.

8. In a method for producing a projection image of the moving material in a volume the steps of;

exciting the spins in a planar region of the volume using an adiabatic fast passage excitation where the excitation frequency is swept through resonance and the spins of static material are inverted;

receiving the signals from the moving nuclei which have not experienced a complete inversion excitation;

repeating the sequence for each planar region of the volume; and processing the signals to produce a two-dimensional projection image of the moving material in the volume.

9. Apparatus for producing a two-dimensional projection image of the moving material in a volume comprising;

means for insensitizing the magnetic spins in a region of the volume using saturation excitation;

means for exciting the spins in the region with a burst so that only moving material which has traveled into the region and not experienced complete saturation will produce an output signal; and means for processing the received output signals to produce a two-dimensional projection image of the body.

10. Apparatus as recited in claim 9 wherein the means for insensitizing the magnetic spins in a planar region of the volume include a first magnetic gradient, parallel to the plane of the two-dimensional projection image, in the presence of a sinusoidal insensitizing signal whose duration is comparable to T1, the spin-lattice relaxation time;

the means for exciting the spins in the planar region include a 90° burst excitation whose duration is short as compared to T1;

the means for receiving and processing output signals from the excited planar region include a second magnetic gradient normal to the first magnetic gradient where each line in the planar region will produce a different frequency and the line integrals are decomposed using a frequency decomposition system; and the means for producing a two-dimensional projection image includes means for repeating the insensitizing and burst excitations using different frequencies representing different planar regions to complete the projection image of the volume.

11. Apparatus for providing a two-dimensional projection image of the moving material in a volume using nuclear magnetic resonance comprising;

means for applying a first magnetic gradient field parallel to the two-dimensional projection image;

means for exciting the nuclear magnetic resonant spins in a planar region of the volume normal to the first gradient field and normal to the two-dimensional projection image;

means for applying a second magnetic gradient field normal to the first magnetic gradient field following the excitation signal during the time that free induction decay signals are received;

means for processing the free induction decay signals to provide a projection of the moving material in the planar region of the volume; and means for repeating the sequence using different excitation signals of different frequencies to excite the spins in different planar regions of the volume to complete the two-dimensional projection of the volume.

12. Apparatus as recited in claim 11 where the means for processing the signal to provide a projection of the moving material includes;

means for exciting the nuclear magnetic resonant spins in each planar region of the volume during a time when the moving material is at a first velocity;

means for exciting the nuclear magnetic resonant spins in each planar region of the volume d ring a time when the moving material is at a second velocity; and means for subtracting the processed signals resulting from the two excitations in each planar region.

13. Apparatus as recited in claim 11 where the excitation means is an inversion excitation whereby all static material produces no free induction decay signals.

14. Apparatus as recited in claim 11 where the excitation means is a sequence of two burst excitations of amplitude and duration such that all static material produces no free induction decay signals following the second burst.

15. Apparatus as recited in claim 11 where the excitation means is a saturation excitation having a duration substantially comparable to T1 followed by an excitation burst of duration shorter that T1 whereby the static material is saturated and fails to produce signals in response to the burst.

16. Apparatus as recited in claim 11 including means for applying an alternating gradient field in the same direction as the first gradient field during the time of the free induction decay signal where the null plane of the alternating gradient field is adjacent to the excited planar region whereby only moving excited nuclei which have traveled into the null plane will produce output signals.

17. Apparatus as recited in claim 16 where the null plane is above the excited planar region whereby only excited nuclei which have moved upward will produce output signals.

18. Apparatus as recited in claim 16 where the null plane is below the excited planar region whereby only excited nuclei which have moved downward will produce output signals.

19. Apparatus for producing a two-dimensional projection image of material flowing in a given direction in a volume comprising;
means for exciting the nuclear magnetic spins in a planar region of the volume;
means for receiving signals from those nuclei which have moved to the upper or lower adjacent plane of the volume;
means for repeating the sequence for all planar regions of the volume; and
means for processing the signals from each planar region to produce a two-dimensional projection image of material which has moved either upward or downward with respect to each planar region.

20. Apparatus as recited in claim 19 wherein the means for exciting the nuclear spins in a planar region of the volume includes a first burst excitation in the presence of a gradient normal to the planar region and the means for receiving signals from nuclei which have moved to an adjacent plane includes an inversion burst excitation of substantially 180° in the presence of the same gradient where the inversion burst excitation is higher or lower in frequency than the first burst excitation depending on whether upward or downward flow is being imaged and said inversion burst excitation produces a spin echo signal which, in the presence of a gradient transverse to the planar region, can be decomposed in frequency to represent the projection lines of that planar region.

21. Apparatus as recited in claim 20 including a second inversion excitation occuring after the first inversion excitation having a frequency such that the two inversion excitations are higher and lower in frequency than the first burst excitation and including means for processing both resultant spin echo signals.

22. Apparatus as recited in claim 19 including means for receiving the signals resulting from the excitation of static material in the planar region of the volume and means for processing these to produce a projection image of the static material.

23. Apparatus as recited in claim 22 wherein the means for receiving and processing the signals from the static material includes means for receiving the FID signal in the presence of a transverse gradient and decomposing the frequency spectrum of the signal to form an array of projection lines.

24. Apparatus as recited in claim 22 including means for combining the static and directional flow projection images.

25. Apparatus as recited in claim 24 wherein the means for combining the static and directional flow projection images includes means for cancelling the residual static image that is present in the flow images.

* * * * *